US010837037B2

(12) United States Patent
Birikh et al.

(10) Patent No.: US 10,837,037 B2
(45) Date of Patent: *Nov. 17, 2020

(54) METHOD FOR CONVERTING GLUCOSE INTO FRUCTOSE IN THE PRESENCE OF LIGNIN

(71) Applicant: METGEN OY, Kaarina (FI)

(72) Inventors: Klara Birikh, Kaarina (FI); Anu Minna Maaret Suonpää, Kaarina (FI); Matti Wilhelm Heikkilä, Kaarina (FI)

(73) Assignee: METGEN OY, Kaarina (FI)

( * ) Notice: Subject to any disclaimer, the term of this patent is extended or adjusted under 35 U.S.C. 154(b) by 0 days.

This patent is subject to a terminal disclaimer.

(21) Appl. No.: 16/311,606

(22) PCT Filed: Jun. 20, 2017

(86) PCT No.: PCT/EP2017/065041
§ 371 (c)(1),
(2) Date: Dec. 19, 2018

(87) PCT Pub. No.: WO2017/220548
PCT Pub. Date: Dec. 28, 2017

(65) Prior Publication Data
US 2019/0185891 A1    Jun. 20, 2019

(30) Foreign Application Priority Data

Jun. 20, 2016 (EP) .................................... 16175234

(51) Int. Cl.
*C12P 19/02*     (2006.01)
*C12P 19/24*     (2006.01)

(52) U.S. Cl.
CPC .............. *C12P 19/02* (2013.01); *C12P 19/24* (2013.01); *C12Y 503/01005* (2013.01); *C12P 2201/00* (2013.01)

(58) Field of Classification Search
None
See application file for complete search history.

(56) References Cited

U.S. PATENT DOCUMENTS

2015/0148267 A1   5/2015  Tjon-Joe-Pin et al.
2015/0361474 A1  12/2015  Nelson et al.

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Accession B5YAD2. Nov. 25, 2008 (Year: 2008).*
Anonymous, "UNIPROT: B5YAD2", Nov. 25, 2008 (Nov. 25, 2008), XP055312140, Retrieved from the Internet: URL: http://ibis.internal.epo.org/exam/dbfetch.jsp?id=UNIPROT:B5YAD2, retrieved on Oct. 19, 2016; sequence.
Anonymous, "UNIPROT: B8E394", Mar. 3, 2009 (Mar. 3, 2009), XP055312190, Retrieved from the Internet: http://ibis.internal.epo.org/exam/dbfetch.jsp?id=UNIPROT:B8E394, retrieved on Oct. 19, 2016; sequence.
"Bergquist, Peter L. et al: ""Selected Enzymes from Extreme Thermophiles with Applications in Biotechnology""", Current Biotechnology, vol. 3, No. 1 2014, pp. 45-59, XP055311686, Retrieved from the Internet: http://content.eurekaselect.com/download.php?param=Sk9VCUk5iBTFFMvQkkVOtL0NkCSUF9ULEzMvtMS8hwMDsA2Qc0JJkT1Q6ucGaRmfaHxhncHBdsaWrNhd, p. 50, left-hand column, paragraph 4-p. 53, left-hand column, paragraph 2".
Bhosale, Snehalata H. et al., "Molecular and Industrial Aspects of Glucose Isomerase Functional Role of Esssential Amino Acid Residues", Microbiological Reviews, vol. 60(2), Jun. 1, 1996 (Jun. 1, 1996), pp. 280-300, XP055311888, Retrieved from the Internet: https://www.ncbi.nlm.nih.gov/pmc/articles/PMC239444/pdf/600280.pdf, [retrieved on Oct. 18, 2016], p. 281, left-hand column, paragraph 1, p. 295, right-hand column, paragraph 3-p. 297, left-hand column, paragraph 2.
Brumm, Phillip J. et al., "The Complete Genome Sequence of Hyperthermophile Dictyoglomus turgidum DSM 6724 (TM) Reveals a Specialized Carbohydrate Fermentor", Frontiers in Microbiology, vol. 7, Dec. 20, 2016 (Dec. 20, 2016), XP055408418, DOI: 10.3389/fmicb.2016.01979; the whole document.
Gibbs, M D et al. "Cloning, Sequencing, and Expression of a Xylanase Gene From the Extreme Thermophile Dictyoglomus Thermophilum Rt46b.1 and Activity of the Enzyme on Fiber-Bound Substrate", Applied and Environmental Microbiology, American Society for Microbiology, US, vol. 61, No. 12, Dec. 1, 1995 (Dec. 1, 1995), pp. 4403-4408, XP000618234, ISSN: 0099-2240 abstract p. 4406, right-hand column, paragraph 2-3 p. 4407, left-hand column, paragraph 3-1.

(Continued)

*Primary Examiner* — Christian L Fronda
(74) *Attorney, Agent, or Firm* — Patent Law Works, LLP (57) ABSTRACT

The invention is in the field of enzymology. More in particular, it provides a method for the isomerization of glucose into fructose wherein the glucose is derived from lignocellulosic material. More in particular, it provides a method for converting glucose into fructose comprising the steps of: providing a composition comprising water, glucose and lignin, enzymatically converting the glucose to fructose in the presence of a glucose isomerase, and optionally purifying the fructose from the solution, wherein the glucose isomerase comprises an amino acid sequence that is at least 90% identical with the sequence according to SEQ ID NO: 1 or SEQ ID NO: 2.

14 Claims, 3 Drawing Sheets

Specification includes a Sequence Listing.

(56) References Cited

OTHER PUBLICATIONS

Kim, Jung-Eun et al. "Characterization of a recombinant cellobiose 2-epimerase from that epimerizes and isomerizes beta-1,4- and alpha1,4-gluco-oligosaccharides", Biotechnology Letters, Springer Netherlands, Dordrecht, vol. 34, No. 11, Jul. 11, 2012 (Jul. 11, 2012), pp. 2061-2068, XP035119597, ISSN: 1573-6776, DOI: 10.1007/S10529-012-0999-Z; abstract p. 2062, right-hand column, paragraph 3, p. 2065, left-hand column, paragraph 2-right-hand column, paragraph 2.
PCT International Search Report and Written Opinion, Application No. PCT/EP2017/065041, dated Sep. 29, 2017, 15 pages.

\* cited by examiner

Relative residual activity [%]

METHOD FOR CONVERTING GLUCOSE INTO FRUCTOSE IN THE PRESENCE OF LIGNIN

FIELD OF THE INVENTION

The invention is in the field of enzymology. More in particular, it provides a method for the isomerization of glucose into fructose wherein the glucose is derived from lignocellulosic material.

BACKGROUND OF THE INVENTION

High-fructose corn syrup (HFCS) (also called glucose-fructose, isoglucose and glucose-fructose syrup) is a sweetener made from corn starch that has been processed by an enzyme called glucose isomerase (EC 5.3.1.5) to convert some of its glucose into fructose. HFCS was first marketed in the early 1970s by the Clinton Corn Processing Company, together with the Japanese research institute where the enzyme was discovered.

As a sweetener, HFCS is often compared to granulated sugar. Advantages of HFCS over granulated sugar include being easier to handle, and being less expensive in some countries. In the U.S., HFCS is among the sweeteners that mostly replaced sucrose (table sugar) in the food industry.

In a contemporary process, corn (maize) is milled to produce corn starch and an "acid-enzyme" process is used in which the corn starch solution is acidified to begin breaking up the existing carbohydrates, and then enzymes are added to further metabolize the starch and convert the resulting sugars to fructose.

Glucose isomerase is an enzyme which converts glucose to fructose in a reversible reaction with equilibrium around 1:1 ratio of glucose to fructose. The enzyme may be obtained from many different species of bacteria such as *Streptomyces, Actinoplanes, Microbacterium* and *Bacillus*, and the enzyme is or has been marketed by companies such as Enzyme Bio-systems, Genencor, Gist-Brocades, Solvay Enzyme Inc and Novo Nordisk.

Most successful commercial glucose isomerases are immobilized and as a consequence are very stable with an extremely long half life. In a typical process, the immobilized isomerase is loaded in a column and substrate (feed stock) is passed through at a rate that produces an effluent containing 42% fructose. Prerequisite however, is that the feed stock is a refined hydrolysate containing 93-96% glucose. Efficient refining is required in order to remove impurities that could cause inactivation of the glucose isomerase.

Glucose may also be obtained from lignocellulose material. Lignocellulose refers to plant dry matter, so called lignocellulosic biomass. It is the most abundantly available raw material on earth for the production of bio-fuels, mainly bio-ethanol. It is composed of carbohydrate polymers (cellulose, hemicellulose), and an aromatic polymer (lignin). These carbohydrate polymers contain different sugar monomers (six and five carbon sugars) and they are tightly bound to lignin.

Alternative enzymes for the conversion of lignocellulose derived glucose to fructose are not yet available but would be highly desirable.

SUMMARY OF THE INVENTION

We found that use of the currently available glucose isomerases in the conversion of lignocellulose-derived glucose into fructose is hampered by impurities that are present in lignocellulose-derived glucose. These impurities lead to a significant decrease in the stability of the enzyme.

We herein present a glucose isomerase that allows to avoid cumbersome and costly purification steps in the production of fructose from lignocellulose material. The glucose isomerase as presented herein is found to be resistant towards some or most, if not all impurities of lignocellulose-derived glucose.

We identified a family of glucose isomerases that are particularly suited for the conversion of glucose to fructose in a process wherein the glucose is derived from a lignocellulose source. Whereas commercial enzymes and other known glucose isomerases are unstable in solutions comprising lignocellulose derived glucose and require extensive purification of the substrate, two different bacterial glucose isomerases derived from the genus of Diktyoglomus are proven herein to be resistant against the decrease in stability when glucose derived from lignocellulosic material or biomass is used as the substrate. We show herein that lignin inhibits or deactivates or destabilizes the conventional glucose isomerases, whereas bacterial glucose isomerases derived from the genus of Diktyoglomus are resistant against that.

Accordingly, the invention relates to a method for converting glucose into fructose comprising the steps of:
 a) providing a composition comprising water, glucose and lignin,
 b) enzymatically converting the glucose to fructose in the presence of a glucose isomerase,
 c) optionally purifying the fructose from the solution,
wherein the glucose isomerase comprises an amino acid sequence that is at least 90% identical with the sequence according to SEQ ID NO: 1 or SEQ ID NO: 2.

DETAILED DESCRIPTION OF THE INVENTION

In enzymology, a glucose isomerase (EC 5.3.1.5) is an enzyme that catalyzes the interconversion of D-glucose and D-fructose. This enzyme belongs to the family of isomerases, specifically those intramolecular oxidoreductases interconverting aldoses and ketoses. The glucose isomerase has now been observed in nearly a hundred species of bacteria. Glucose-isomerases are also commonly called xylose-isomerases due to their use in the industry to produce xylulose from xylose. The systematic name of this enzyme class is D-xylose aldose-ketose-isomerase. Other names in common use include D-xylose isomerase, D-xylose ketoisomerase, and D-xylose ketol-isomerase.

The commercially available glucose isomerase enzymes have been used successfully in the production of high fructose corn syrup (HFCS) but they are not suited for the isomerisation of glucose obtained from lignocellulose material. Such lignocellulose derived glucose is characterized by the presence of lignin and other sugars derived from hemicelluloses.

Lignin is a complex organic material comprising cross-linked phenolic polymers. In spite of its structural diversity, it has a characteristic absorption spectrum in UV range with a peak at 280 nm, which is often used to quantify lignin content. Conveniently, sugars, such as monosaccharides, disaccharides, polysaccharides and hemicelluloses do not have an absorption in UV range.

Moreover, lignocellulose-derived glucose is usually obtained in rather low concentration (typically in the order of 2-5%) whereas HFCS is produced from feed stock containing between 30% and 40% of glucose (of 93-96% purity). Therefore, concentrating lignocellulosic hydrolysate to achieve such high sugar levels will result in a dramatic increase in the concentration of potential inhibitors, making the task of purifying glucose particularly challenging.

We developed an assay to determine the inactivation and stability of glucose isomerase (GI) enzymes and found that commercially available GIs were quickly inactivated in a solution containing lignocellulose-derived glucose at isomerization reaction conditions, and that many other GIs from bacterial origin were unstable as well. As a representative example, the results obtained with a GI obtained from *Thermotoga Neapolitana* (SEQ ID NO: 3) and the widely used GI Sweetzyme® commercially available from Novozymes are shown herein. The Novozymes GI enzyme is derived from *Streptomyces murinus*; a prototype sequence of a GI from that organism is provided herein as SEQ ID NO: 7.

Surprisingly, we found that two different GIs, derived from *Dictyoglomus thermophilum* and *Dictyoglomus turgidum* (SEQ ID NO: 1 and SEQ ID NO: 2, respectively) were stable in lignocellulose-derived glucose solutions and are therefore exceptionally suited for the conversion of lignocellulose-derived glucose into fructose. These GIs are referred herein further as GI1 and GI2.

Glucose isomerases according to SEQ ID NO: 1 and SEQ ID NO: 2 are homologous sequences with a sequence identity of 98%. It may therefore be expected that closely related GIs, such as GIs with an amino acid sequence that is at least 90%, such as 91%, 92%, 93%, 94%, 95%, 96%, or 97% identical with either SEQ ID NO: 1 or SEQ ID NO: 2, will perform in the same way as GI1 and GI2 exemplified herein. Such close homologues may be obtained from natural sources or by directed mutagenesis. The skilled person is well aware of materials and methods for obtaining such close homologues.

As used herein, the degree of identity between two or more amino acid sequences is equivalent to a function of the number of identical positions shared by the sequences; i.e., % identity=number of identical positions divided by the total number of aligned positions×100, excluding gaps, which need to be introduced for optimal alignment of the two sequences, and overhangs. The alignment of two sequences is to be performed over the full length of the polypeptides.

The comparison (aligning) of sequences is a routine task for the skilled person and can be accomplished using standard methods known in the art. For example, a freeware conventionally used for this purpose is "Align" tool at NCBI recourse http://blast.ncbi.nlm.nih.gov/Blast.cgi?PAGE_TYPE=BlastSearch&BLAST_SPEC=blast2seq&LI NK_LOC=align2seq. Other commercial and open software such as Vector NTI are also suitable for this purpose.

The enzymes that did not retain their stability in lignocellulose-derived glucose substrates (GI3 and Sweetzyme®) had amino acid sequences that were completely unrelated to the sequences provided in SEQ ID NO: 1 and SEQ ID NO: 2. A prototype sequence of a GI from *Streptomyces murinus* (Sweetzyme®) was about 26% identical over 77% of its sequence length whereas the sequence of GI3 can only be aligned with the sequence of GI1 over 44% of the length of the sequences and has 29% identity in that region.

Figure 1:
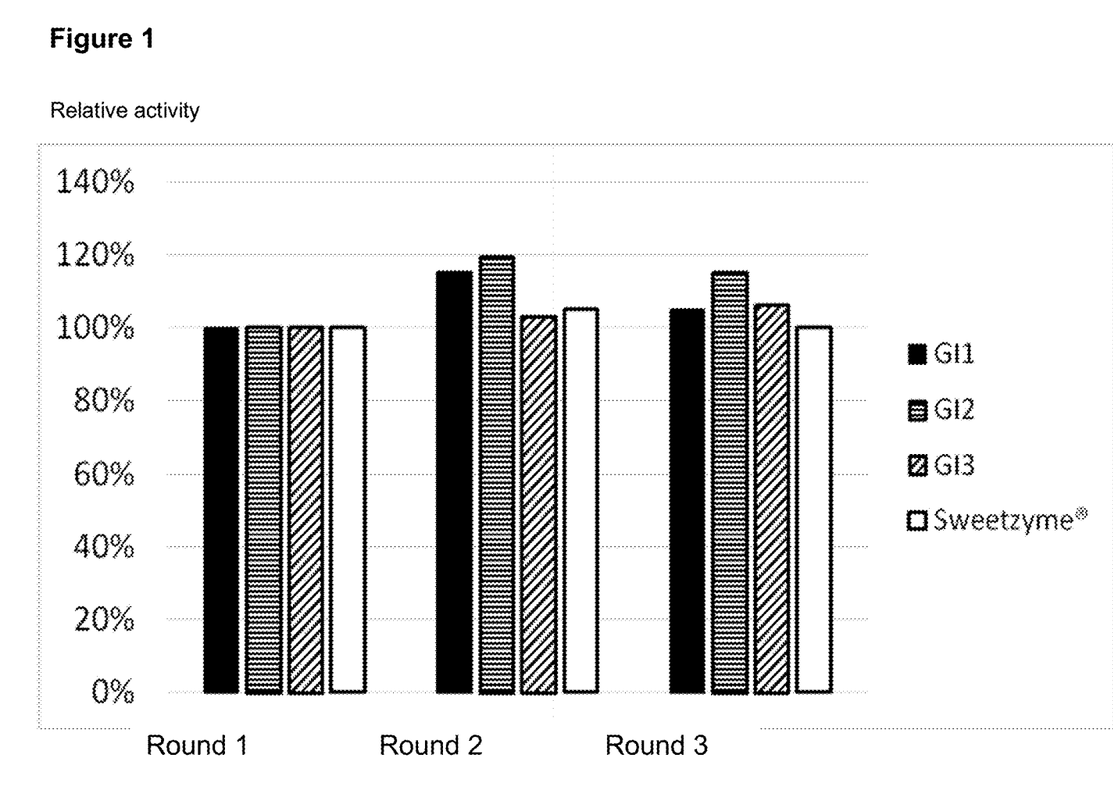
FIG. 1: Diagram showing the stability of 4 different glucose isomerases upon 3 consecutive incubations in a pure glucose substrate.
Figure 2:
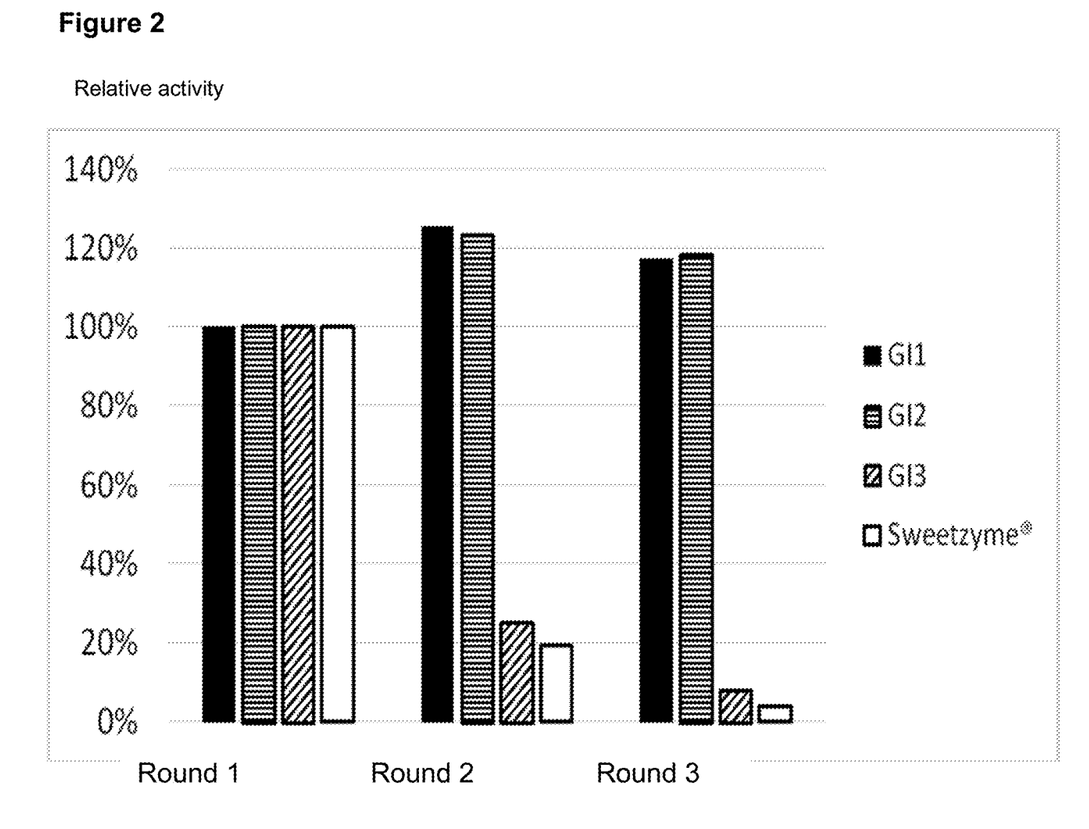
FIG. 2: Diagram showing the stability of 4 different glucose isomerases upon 3 consecutive incubations in a lignocellulose-derived glucose substrate.

Whereas all enzymes tested were still fully active in a solution comprising pure glucose (FIG. 1, example 4), incubation of the enzymes with lignocellulose-derived glucose, containing approximately 8 gram per liter lignin (A280 of 130), revealed that GI1 and GI2 were superior in that they were not inactivated by the presence of such concentrations of lignin (FIG. 2, example 6). In contrast, it was shown that the commercial enzyme and GI3 retained at most 25% of their activity after 2 hours of incubation at 80 degrees Celsius at pH 8.0 and were almost completely inactive after 3 hours under these conditions (FIG. 2). Repeat experiments with comparable lignin content in the order of 5-10 grams per liter showed the same results.

Figure 3:
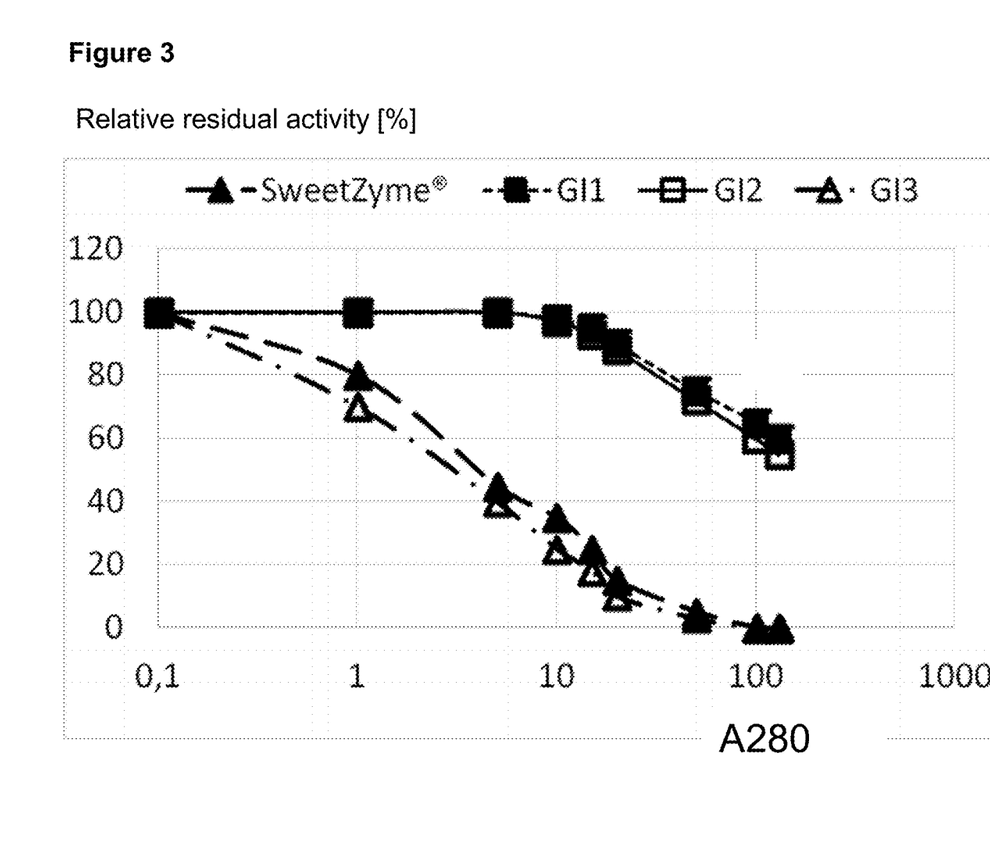
FIG. 3: Graph showing the relative residual activity of 4 different glucose isomerases after 20 hours of incubation with a substrate comprising lignocellulose-derived glucose at 80 degrees Celsius, as a function of lignin content (A280).

In an experiment wherein the residual activity of GIs was determined in the presence of varying concentrations of lignin, it was shown that upon incubation of the GIs for 20 hours at 80 degrees Celsius, GI3 and Sweetzyme® were inactivated for more than 20% already at concentrations of lignin corresponding to an A280 of 1.0 (0.06 gram lignin per liter of substrate, FIG. 3, table 1).

At an A280 of 100 (substrate containing 6 gram lignin per liter) the commercial enzyme and GI3 were completely inactivated after 20 hours at 80 degrees Celsius, whereas GI1 and GI2 still retained more than 50% of their activity (FIG. 3, table 1). When commercially available Kraft lignin from hard or soft wood (solubilized in MOPS buffer pH 8.0) was used instead of hydrolysate, similar results were obtained.

Without wanting to be bound by theory, we speculate that lignin, present in the lignocellulose-derived glucose solution causes the loss in stability of the commercial GIs as well as GI3 as tested herein. Lignocellulose-derived glucose also contains other hemicellulose-derived sugars than glucose, but these were found not to inhibit the commercial GI nor GI3 as tested herein.

Hence, the invention relates to a method for the interconversion of D-glucose and D-fructose in the presence of a glucose isomerase, wherein the D-glucose is derived from lignocellulose-containing biomass, and wherein the glucose isomerase comprises an amino acid sequence that is at least 90% identical with the sequence according to SEQ ID NO: 1 or SEQ ID NO: 2.

The phrase "glucose derived from lignocellulose-containing material" is equivalent to the term "lignocellulose-derived glucose". Both are used herein to indicate that the glucose is contained in a solution comprising a residual amount of lignin, derived from the lignocellulosic material, such as lignocellulosic biomass. As such, the term is used to distinguish the glucose from purified glucose, which does not contain lignin.

GI1 and GI2 as disclosed herein and their homologues with at least 90% sequence identity provide advantageous results in comparison to other GIs. In particular in conditions wherein the substrate solution comprises at least 0.06 gram per liter of lignin (A280 of 1.0), such as 0.3 gram lignin per liter (A280 of 5.0) or even 0.6 gram per liter (A280 of 10).

In other terms, the invention relates to a process for converting glucose into fructose comprising the steps of:
  a) providing a composition comprising water, glucose and lignin, b) enzymatically converting the glucose to fructose in the presence of a glucose isomerase, c) optionally purifying the fructose from the solution, wherein the glucose isomerase comprises an amino acid sequence that is at least 90% identical with the sequence according to SEQ ID NO: 1 or SEQ ID NO: 2.

In a preferred embodiment, the lignin is present in the composition in a concentration of at least 0.06 gram per liter. This corresponds to an absorbance at 280 nm of at least 1.0.

The composition comprising water, glucose and lignin may advantageously be obtained by hydrolyzing a composition comprising lignin, cellulose and/or hemicellulose. Such hydrolysis is advantageously performed enzymatically, for instance by employing a cellulase.

The composition comprising lignin, cellulose and/or hemicellulose may advantageously be obtained from lignocellulose-containing material, such as biomass, such as wood, wood pulp or pretreated biomass or pretreated wood. Advantageously, the pretreatment step comprises a steam explosion step and/or an acid pretreatment step.

All these steps are well known in the art and the skilled person is well aware of the metes and bounds of the terms used herein.

EXAMPLES

Example 1: Preparation of a Polypeptide According to SEQ ID NO: 1, 2 or 3

The DNA constructs encoding the polypeptides according to SEQ ID NO: 1, SEQ ID NO: 2 or SEQ ID NO: 3 were designed using codon frequencies optimized for expression in *E. coli* and commercially synthesized and cloned into a plasmid vector based on a standard pET28a+ plasmid. The plasmid vector contained a nucleotide sequence encoding peptidyl-prolyl isomerase (PPlase) from Enterobacteriaceae (Protein databank accession number WP_000255997.1). This nucleotide sequence encodes an N-terminal tag to the expressed protein. The recombinant gene was expressed in *Escherichia coli* BL21(DE3) under the control of the T7-RNA-polymerase promoter. This resulted in expression of a protein comprising SEQ ID NO: 1, 2 or 3. Nucleotide sequences encoding the glucose isomerases according to SEQ ID NO: 1, 2 and 3 are provided herein as SEQ ID NO: 4, SEQ ID NO: 5 and SEQ ID NO: 6 respectively.

Example 2: Heterologous Expression of Polypeptides with Glucose Isomerase Activity Protein production was carried out in *E. coli* BL21(DE3) strain according to the plasmid manufacturer protocol available at http://richsingiser.com/4402/Novagen%20pET%20system%20manual.pdf. The incubation temperature for protein production was 30 degrees Celsius, which was found optimal for maximum yield of the active protein. Cells were lysed by suspending the cell pellet in lysis buffer (50 mM Tris-HCl pH7.4, 1% Triton×100, 1 mM CoCl2) and heating at 70 degrees Celsius for 30 min. The glucose isomerase activity was detected in the insoluble fraction only, and could be fully recovered by centrifugation. Thus, thermostable recombinant glucose isomerase was expressed in active insoluble form allowing reuse of the enzyme in several reaction batches.

Example 3: Glucose Isomerase Activity Assay

Glucose isomerase activity (isomerization reaction rate) was determined by measuring fructose level in the reaction mixture according to the protocol described in Schenk and Bisswanger, A microplate assay for D-xylose/D-glucose isomerase. Enzyme and Microbial Technology (Elsevier Science Inc, N Y, 1998), V22, pp. 721-723.

Measurement was performed in the linear stage of the reaction course (product accumulation is linear with time). Ten-microliter aliquots of the reaction mixture were taken and pipette into a 96-well plate, 40 ul of water was added resulting in 50 ul sample. In some cases, higher dilution of the reaction mixture with water was used to prepare 50 ul of the diluted sample to match the dynamic range of the method. 150 ul of a freshly prepared 1:1 mixture (v/v) of solution A (0.05% resorcinol in ethanol) and solution B (0.216 g FeNH4(SO4)2*12H2O in 1 l concentrated HCl) were added. For color development, the plate was incubated at 80° C. for 40 min. The absorbance was measured with a microplate reader (Thermo) at 490 nm.

Example 4 Glucose Isomerization Activity of Polypeptides Comprising SEQ ID NO: 1, 2 or 3 and Commercial Glucose Isomerase Sweetzyme® in Pure Glucose Solution In this experiment, we compared four glucose isomerases:
(1) recombinant GI1 (SEQ ID NO: 1) produced in *E. coli*,
(2) recombinant GI2 (SEQ ID NO: 2) produced in *E. coli*,
(3) recombinant GI3 (SEQ ID NO: 3) produced in *E. coli*, and
(4)) glucose isomerase Sweetzyme® (commercial product of Novozymes).

Enzymatic activity was first determined in a glucose solution (100 mM Glucose, 10 mM MOPS pH 8.0, 1 mM MgCl2), this is also referred to herein as "pure glucose solution" or "pure glucose substrate".

Sweetzyme® glucose isomerase was dosed at 0.4 activity units/mL. Dosages of other glucose isomerases according to SEQ ID NO: 1, 2 or 3 were adapted to achieve the same conversion rate as Sweetzyme® in pure glucose solution under the same conditions (pH=8.0, at 80 degrees Celsius).

The amount of enzyme was selected so that during the reaction time the product formation remains linear. GI1 GI2 and GI3 proteins corresponding to SEQ ID NO: 1, 2 and 3 respectively, were in the form of suspension of insoluble active aggregates. Sweetzyme® is an immobilized enzyme appearing as small beads.

To test the stability of the enzymes, three consecutive rounds of incubation were performed with pure glucose solution as the substrate. In the first round, after one hour of reaction time, the enzymes showed almost identical activity (FIG. 1). The enzymes were then recovered by centrifugation and after removal of the supernatant, subjected to a second round of incubation with the pure glucose substrate as following.

Fresh pure glucose substrate (105 mM Glucose, 10 mM MOPS pH 8.0, 1 mM MgCl2) was then added to the pellets containing the enzymes, pellets were re-suspended and reactions were allowed to continue for another hour. After that, enzymes were recovered again and a third round of incubation with pure glucose substrate was carried out the same way. Supernatants from all three reactions with each enzyme were analyzed for fructose concentration to determine enzyme activity.

FIG. 1 shows the enzyme activities of all four enzyme preparations in the three consecutive rounds.

It can be concluded from this that all four enzyme preparations remain active at 80 degrees Celsius for at least 3 hours without losing any activity, and that all four enzyme preparations can be fully recovered from the mixtures by centrifugation and reused.

Example 5 Preparation of Lignocellulose Hydrolysate

Wood chips, obtained from spruce, were submerged in 2% sulfuric acid at a dry matter content of 20% and subjected to a steam explosion pretreatment essentially as described in EP2623607A1. The pretreated material in its entirety (without removing solubilized fractions of hemicellulose and lignin) was subjected to enzymatic hydrolysis using Cellic® CTec3 cellulase product from Novozymes. The hydrolysis was carried out under the manufacturer's recommended conditions (incubation for 72 h at 55 degrees Celsius, pH 5.5 at 10% solids content). The resulting mixture contained 21 g/L Glucose (106 mM), 5.5 g/L Mannose, 1.7 g/L Arabinose and approximately 15 g/L lignin.

Before the isomerization reaction, remaining solids were removed from the hydrolysis mixture by centrifugation (resulting in about 8 g/L remaining lignin concentration) and the pH was adjusted to 8 with sodium hydroxide. The resulting solution is referred to herein further as "hydrolysate" or "lignocellulose hydrolysate" and used for the isomerization reaction.

Example 6 Glucose Isomerization Activity of Polypeptides Comprising SEQ ID NO: 1, 2 or 3 and Commercial Glucose Isomerase Sweetzyme® in Lignocellulose Hydrolysate In this experiment, we compared four glucose isomerases:
(1) recombinant GI1 (SEQ ID NO: 1) produced in *E. coli*,
(2) recombinant GI2 (SEQ ID NO: 2) produced in *E. coli*,
(3) recombinant GI3 (SEQ ID NO: 3) produced in *E. coli*, and
(4)) glucose isomerase Sweetzyme® (commercial product of Novozymes) in an identical set-up as described in Example 4, only this time with the lignocellulose hydrolysate instead of the pure glucose as the substrate.

For this purpose, the lignocellulose substrate was brought to 10 mM MOPS pH 8.0 and 1 mM MgCl2. This substrate solution contained the same glucose concentration as the pure glucose solution used in Example 4. The only difference between the substrate of Example 4 and the substrate described in this Example is that the lignocellulose hydrolysate additionally contained other sugars derived from hemicellulose and lignin.

It was observed that GI1 and GI2 were stable in the lignocellulose substrate for at least three consecutive rounds, whereas GI3 and Sweetzyme® were quickly deteriorating from round to round and eventually became inactive (FIG. 2).

Example 7: Determination of Liqnin Content of Substrate

Lignin content of the lignocellulose-derived substrate was determined by measuring the absorbance at 280 nm (A280), wherein an A280 of 1.0 corresponds to a lignin concentration of 0.06 gram per liter.

Example 8: Enzyme Stability as a Function of Liqnin Content of Substrate

In this experiment, we compared the stability of four glucose isomerases:
(1) recombinant GI1 (SEQ ID NO: 1) produced in *E. coli*,
(2) recombinant GI2 (SEQ ID NO: 2) produced in *E. coli*,
(3) recombinant GI3 (SEQ ID NO: 3) produced in *E. coli*, and
(4)) glucose isomerase Sweetzyme® (commercial product of Novozymes).

Equivalent amounts of these 4 enzymes were added to a solution comprising 105 mM glucose and varying concentrations of lignin (as measured by absorbance at 280 nm (A280)) and incubated for 20 hours at 80 degrees Celsius.

In detail: lignocellulose hydrolysate with an A280 of 130 was diluted with a solution of 105 mM glucose to obtain substrate solutions with the same amount of glucose (105 mM) and varying concentrations of lignin as measured by absorbance at 280 nm. All substrate solutions were brought to 10 mM MOPS pH 8.0 and 1 mM MgCl2. In that way, identical substrate solutions with a varying lignin content corresponding to an A280 of 0.1 to 130 were obtained. The substrate solutions contained equivalent amounts of glucose isomerase activity as measured using pure glucose as described in example 4.

Incubation was carried out at 80 degrees Celsius for 20 h. Afterwards, the enzyme was recovered and tested for residual activity on pure glucose substrate. Residual activities are shown in table 1 below and in FIG. 3 on a logarithmic scale.

It was found that a substrate containing lignin in an amount corresponding to an A280 of 1.0 (0.06 gram of lignin per liter) already inactivated the commercial enzyme Sweetzyme® and GI3 for more than 20%, whereas the enzymes GI1 and GI2 remained 100% active until a concentration corresponding to an A280 of at least 5 (0.3 gram of lignin per liter). At a lignin content corresponding to an A280 of 100 (6 gram per liter) the commercial enzyme Sweetzyme® and GI3 were completely inactive, whereas GI1 and GI2 retained still at least 60% of their activity.

TABLE 1 relative residual activity of 4 different GIs as a function of substrate lignin content

| A280 | Sweetzyme (R) | GI1 | GI2 | GI3 |
| --- | --- | --- | --- | --- |
| 0.1 | 100 | 100 | 100 | 100 |
| 1 | 80 | 100 | 100 | 70 |
| 5 | 45 | 100 | 100 | 40 |
| 10 | 35 | 98 | 97 | 30 |
| 15 | 25 | 95 | 93 | 18 |
| 20 | 15 | 90 | 88 | 10 |
| 50 | 5 | 75 | 72 | 3 |
| 100 | 0 | 65 | 60 | 0 |
| 130 | 0 | 60 | 55 | 0 |

The invention claimed is:

1. A method of converting glucose into fructose, the method comprising:
   providing a composition comprising water, glucose and at least 0.06 grams per liter lignin, and
   enzymatically converting the glucose in the composition to fructose with a glucose isomerase,
   wherein the glucose isomerase comprises an amino acid sequence having at least 95% identity with SEQ ID NO: 1 or SEQ ID NO: 2;and
   wherein the glucose isomerase is in fluid contact with the lignin.

2. The method according to claim 1, wherein the composition has an absorbance at 280 nm of at least 1.0.

3. The method according to claim 1, wherein providing the composition comprises providing pretreated lignocellulose-containing material.

4. The method according to claim 3, wherein providing the pretreated lignocellulose-containing material comprises hydrolysis of lignocellulose-containing material.

5. The method according to claim 4, wherein the hydrolysis is enzymatic hydrolysis.

6. The method according to claim 5, wherein the enzymatic hydrolysis is performed using a cellulase.

7. The method according to claim 3, wherein the lignocellulose- containing material is biomass.

8. The method according to claim 7, wherein the biomass is wood or wood pulp.

9. The method according to claim 8, wherein the wood is soft wood.

10. The method according to claim 1, further comprising purifying the fructose from the composition after the conversion of glucose to fructose.

11. A method of converting glucose into fructose, the method comprising:
    providing a composition comprising water, glucose and lignin, and
    enzymatically converting the glucose in the composition to fructose with a glucose isomerase,
    wherein the glucose isomerase comprises an amino acid sequence having at least 95% identity with SEQ ID NO: 1 or SEQ ID NO: 2; and
    wherein the glucose isomerase has the same activity in the presence of 0.3 grams per liter lignin as it does in the presence of 0.006 grams per liter lignin.

12. The method according to claim 11, wherein the composition comprises at least 0.3 grams per liter lignin.

13. A method of converting glucose into fructose, the method comprising:
    providing a composition comprising water, glucose, and lignin, and
    enzymatically converting the glucose in the composition to fructose with a glucose isomerase,
    wherein the glucose isomerase comprises an amino acid sequence having at least 95% identity with SEQ ID NO: 1 or SEQ ID NO: 2; and
    wherein the glucose isomerase has the same activity in the presence of 0.06 grams per liter lignin as it does in the presence of 0.006 grams per liter lignin.

14. The method according to claim 13, wherein the composition comprises at least 0.06 grams per liter lignin.

* * * * *

SEQUENCE LISTING

<160> NUMBER OF SEQ ID NOS: 7

<210> SEQ ID NO 1
<211> LENGTH: 368
<212> TYPE: PRT
<213> ORGANISM: Dictyoglomus thermophilum

<400> SEQUENCE: 1

```
Met Pro Phe Val Asp His Arg Ala Gln Lys Ile Arg Arg Ser Lys Glu
1               5                   10                  15

Glu Leu Leu Lys His Met Gln Thr Phe Lys Leu Asp Leu Lys Phe Ser
            20                  25                  30

Val Gly Ile Trp Tyr Phe Thr Pro Gly Gly Arg Phe His Glu Pro
        35                  40                  45

Tyr Val Glu Gln Lys Ser Ile Pro Glu Arg Ile Glu Met Ala Ala Glu
    50                  55                  60

Met Ala Lys Phe Gly Val Lys Gly Ile Glu Ala His Tyr Pro Ala Glu
65                  70                  75                  80

Val Asn Glu Glu Asn Leu His Leu Tyr Lys Gln Leu Glu Lys Glu Ala
                85                  90                  95

Gly Ile Arg Leu Val Ala Val Pro Leu Ser Leu Phe Tyr Asp Lys Ile
            100                 105                 110

Phe Glu Phe Gly Ser Leu Ser Asn Pro Tyr Glu Lys Tyr Arg Lys Val
        115                 120                 125

Ala Tyr Glu Arg Leu Val Asn Gly Leu Lys Leu Val Lys Glu Ala Asn
    130                 135                 140

Ala Asp Ile Cys Ile Ile Trp Pro Gly Ile Asp Gly Tyr Thr Tyr Ser
145                 150                 155                 160

Tyr Gly His Leu Tyr Tyr His Met Trp Asp Thr Phe Glu Glu Leu Val
                165                 170                 175

Ala Gln Ala Met Asp Glu Val Pro Gly Val Gln Val Ala Ile Glu Pro
            180                 185                 190

Lys Pro Tyr Glu Pro Ala Pro Asn Asn Ile Tyr Arg Thr Thr Ala Asp
        195                 200                 205

Gly Ile Leu Ala Ala Arg Asp Ile Glu Ala Arg Leu Lys Asn Pro Glu
    210                 215                 220

Asn Leu Lys Leu Leu Gln Glu Gly His Ala Leu Val Gly Leu Asn Pro
225                 230                 235                 240

Glu Val Gly His Val Arg Met Gly Phe Glu Asp Leu Pro Tyr Ala Tyr
                245                 250                 255

Ala Arg Val Ala Arg Glu Gly Arg Leu Phe His Thr His Trp Asn Ser
            260                 265                 270

Gln Pro Leu Gly Asn Tyr Asp Gln Asp Leu Asn Ile Gly Val Val Asp
        275                 280                 285

Trp Asp Ser Thr Glu Ala Leu Leu Tyr Thr Leu Lys Met Val Gly Tyr
    290                 295                 300

Gln Gly Tyr Phe Gly Ile Asp Ile Asn Pro Glu Arg Met Pro Val Ile
305                 310                 315                 320

Lys Ala Ile Glu Ile Asn Thr Lys Val Leu Gln Ile Met Asn Glu Arg
                325                 330                 335

Ile Glu Arg Leu Pro His Asp Arg Ile Glu Cys Tyr Phe Asp Pro
            340                 345                 350

Glu Asn His Arg Gly Glu Leu Glu Leu Ile Leu Ala Glu Asn His Lys
        355                 360                 365
```

```
<210> SEQ ID NO 2
<211> LENGTH: 368
<212> TYPE: PRT
<213> ORGANISM: Dictyoglomus turgidum

<400> SEQUENCE: 2

Met Pro Phe Val Asp His Arg Asn Gln Lys Ile Arg Arg Ser Lys Glu
 1               5                  10                  15

Glu Leu Leu Lys His Met Gln Thr Phe Lys Leu Asp Leu Lys Phe Ser
             20                  25                  30

Val Gly Ile Trp Tyr Phe Thr Pro Gly Gly Arg Phe His Glu Pro
         35                  40                  45

Tyr Val Glu Gln Lys Gly Ile Pro Glu Arg Ile Glu Met Ala Ala Glu
     50                  55                  60

Met Ala Lys Tyr Gly Val Lys Gly Ile Glu Ala His Tyr Pro Ala Glu
 65                  70                  75                  80

Val Asn Glu Glu Asn Leu His Leu Tyr Lys Gln Leu Glu Lys Glu Thr
                 85                  90                  95

Gly Ile Arg Leu Val Ala Val Pro Leu Ser Leu Phe Tyr Asp Lys Ile
            100                 105                 110

Phe Glu Phe Gly Ser Leu Ser Asn Pro Tyr Glu Lys Tyr Arg Lys Ile
        115                 120                 125

Ala Tyr Glu Arg Leu Val Asn Gly Leu Lys Leu Val Lys Glu Ala Asn
130                 135                 140

Ala Asp Ile Cys Ile Ile Trp Pro Gly Ile Asp Gly Tyr Thr Tyr Ser
145                 150                 155                 160

Tyr Gly His Leu Tyr Tyr His Met Trp Asp Thr Phe Glu Glu Leu Val
                165                 170                 175

Ala Gln Ala Met Asp Glu Val Pro Gly Val Gln Val Ala Ile Glu Pro
            180                 185                 190

Lys Pro Tyr Glu Pro Ala Pro Asn Asn Ile Tyr Arg Thr Thr Ala Asp
        195                 200                 205

Gly Ile Leu Ala Ala Arg Asp Ile Glu Ala Arg Leu Lys Asn Pro Glu
210                 215                 220

Asn Leu Lys Leu Leu Gln Glu Gly His Ala Leu Val Gly Leu Asn Pro
225                 230                 235                 240

Glu Val Gly His Val Arg Met Gly Phe Glu Asp Leu Pro Tyr Ala Tyr
                245                 250                 255

Ala Arg Val Ala Arg Glu Gly Arg Leu Phe His Thr His Trp Asn Ser
            260                 265                 270

Gln Pro Leu Gly Asn Tyr Asp Gln Asp Leu Asn Ile Gly Val Val Asp
        275                 280                 285

Trp Asp Ser Thr Glu Ala Leu Tyr Thr Leu Lys Met Val Gly Tyr
290                 295                 300

Gln Gly Tyr Phe Gly Ile Asp Ile Asn Pro Glu Arg Ile Pro Val Val
305                 310                 315                 320

Lys Ala Ile Glu Ile Asn Thr Lys Val Leu Gln Ile Met Asn Glu Arg
                325                 330                 335

Ile Glu Arg Leu Pro His Asp Arg Ile Ile Glu Cys Tyr Phe Asp Pro
            340                 345                 350

Glu Asn His Arg Gly Glu Leu Glu Leu Ile Leu Ala Glu Asn His Arg
        355                 360                 365

<210> SEQ ID NO 3
```

```
<211> LENGTH: 444
<212> TYPE: PRT
<213> ORGANISM: Thermotoga Neapolitana

<400> SEQUENCE: 3
```

| | | | | | | | | | | | | | | |
|---|---|---|---|---|---|---|---|---|---|---|---|---|---|---|
| Met | Ala | Glu | Phe | Phe | Pro | Glu | Ile | Pro | Lys | Val | Gln | Phe | Glu | Gly | Lys |
| 1 | | | | 5 | | | | | 10 | | | | | 15 | |
| Glu | Ser | Thr | Asn | Pro | Leu | Ala | Phe | Lys | Phe | Tyr | Asp | Pro | Glu | Glu | Ile |
| | | | 20 | | | | | 25 | | | | | 30 | | |
| Ile | Asp | Gly | Lys | Pro | Leu | Lys | Asp | His | Leu | Lys | Phe | Ser | Val | Ala | Phe |
| | | | 35 | | | | | 40 | | | | | 45 | | |
| Trp | His | Thr | Phe | Val | Asn | Glu | Gly | Arg | Asp | Pro | Phe | Gly | Asp | Pro | Thr |
| | | 50 | | | | | 55 | | | | | 60 | | | |
| Ala | Asp | Arg | Pro | Trp | Asn | Arg | Tyr | Thr | Asp | Pro | Met | Asp | Lys | Ala | Phe |
| 65 | | | | | 70 | | | | | 75 | | | | | 80 |
| Ala | Arg | Val | Asp | Ala | Leu | Phe | Glu | Phe | Cys | Glu | Lys | Leu | Asn | Ile | Glu |
| | | | | 85 | | | | | 90 | | | | | 95 | |
| Tyr | Phe | Cys | Phe | His | Asp | Arg | Asp | Ile | Ala | Pro | Glu | Gly | Lys | Thr | Leu |
| | | | 100 | | | | | 105 | | | | | 110 | | |
| Arg | Glu | Thr | Asn | Lys | Ile | Leu | Asp | Lys | Val | Val | Glu | Arg | Ile | Lys | Glu |
| | | | 115 | | | | | 120 | | | | | 125 | | |
| Arg | Met | Lys | Asp | Ser | Asn | Val | Lys | Leu | Leu | Trp | Gly | Thr | Ala | Asn | Leu |
| | | 130 | | | | | 135 | | | | | 140 | | | |
| Phe | Ser | His | Pro | Arg | Tyr | Met | His | Gly | Ala | Ala | Thr | Thr | Cys | Ser | Ala |
| 145 | | | | | 150 | | | | | 155 | | | | | 160 |
| Asp | Val | Phe | Ala | Tyr | Ala | Ala | Ala | Gln | Val | Lys | Lys | Ala | Leu | Glu | Ile |
| | | | | 165 | | | | | 170 | | | | | 175 | |
| Thr | Lys | Glu | Leu | Gly | Gly | Glu | Gly | Tyr | Val | Phe | Trp | Gly | Gly | Arg | Glu |
| | | | 180 | | | | | 185 | | | | | 190 | | |
| Gly | Tyr | Glu | Thr | Leu | Leu | Asn | Thr | Asp | Leu | Gly | Phe | Glu | Leu | Glu | Asn |
| | | | 195 | | | | | 200 | | | | | 205 | | |
| Leu | Ala | Arg | Phe | Leu | Arg | Met | Ala | Val | Asp | Tyr | Ala | Lys | Arg | Ile | Gly |
| | | 210 | | | | | 215 | | | | | 220 | | | |
| Phe | Thr | Gly | Gln | Phe | Leu | Ile | Glu | Pro | Lys | Pro | Lys | Glu | Pro | Thr | Lys |
| 225 | | | | | 230 | | | | | 235 | | | | | 240 |
| His | Gln | Tyr | Asp | Phe | Asp | Val | Ala | Thr | Ala | Tyr | Ala | Phe | Leu | Lys | Ser |
| | | | | 245 | | | | | 250 | | | | | 255 | |
| His | Gly | Leu | Asp | Glu | Tyr | Phe | Lys | Phe | Asn | Ile | Glu | Ala | Asn | His | Ala |
| | | | 260 | | | | | 265 | | | | | 270 | | |
| Thr | Leu | Ala | Gly | His | Thr | Phe | Gln | His | Glu | Leu | Arg | Met | Ala | Arg | Ile |
| | | | 275 | | | | | 280 | | | | | 285 | | |
| Leu | Gly | Lys | Leu | Gly | Ser | Ile | Asp | Ala | Asn | Gln | Gly | Asp | Leu | Leu | Leu |
| | | 290 | | | | | 295 | | | | | 300 | | | |
| Gly | Trp | Asp | Thr | Asp | Gln | Phe | Pro | Thr | Asn | Val | Tyr | Asp | Thr | Thr | Leu |
| 305 | | | | | 310 | | | | | 315 | | | | | 320 |
| Ala | Met | Tyr | Glu | Val | Ile | Lys | Ala | Gly | Gly | Phe | Thr | Lys | Gly | Gly | Leu |
| | | | | 325 | | | | | 330 | | | | | 335 | |
| Asn | Phe | Asp | Ala | Lys | Val | Arg | Arg | Ala | Ser | Tyr | Lys | Val | Glu | Asp | Leu |
| | | | 340 | | | | | 345 | | | | | 350 | | |
| Phe | Ile | Gly | His | Ile | Ala | Gly | Met | Asp | Thr | Phe | Ala | Leu | Gly | Phe | Lys |
| | | | 355 | | | | | 360 | | | | | 365 | | |
| Val | Ala | Tyr | Lys | Leu | Val | Lys | Asp | Gly | Val | Leu | Asp | Lys | Phe | Ile | Glu |
| | | 370 | | | | | 375 | | | | | 380 | | | |
| Glu | Lys | Tyr | Arg | Ser | Phe | Arg | Glu | Gly | Ile | Gly | Arg | Asp | Ile | Val | Glu |

```
                385            390            395            400
        Gly Lys Val Asp Phe Glu Lys Leu Glu Glu Tyr Ile Ile Asp Lys Glu
                        405                410                415

Thr Ile Glu Leu Pro Ser Gly Lys Gln Glu Tyr Leu Glu Ser Leu Ile
                        420                425                430

Asn Ser Tyr Ile Val Lys Thr Ile Leu Glu Leu Arg
                        435                440

<210> SEQ ID NO 4
<211> LENGTH: 1107
<212> TYPE: DNA
<213> ORGANISM: Dictyoglomus thermophilum

<400> SEQUENCE: 4
atgccgtttg ttgatcatcg tgcacagaaa attcgtcgca gcaaagaaga actgctgaaa        60
catatgcaga ccttcaaact ggatctgaaa tttagcgtgg gcatctggta ttttacaccg       120
ggtggtggtc gttttcatga accgtatgtt gaacagaaaa gcattccgga acgtattgaa       180
atggcagcag aaatggcaaa atttggcgtg aaaggtattg aagcacatta tccggctgaa       240
gtgaatgaag aaaatctgca cctgtataaa cagctggaaa agaagcaggt attcgtctg        300 gttgcagttc cgctgagcct gttttatgat aaaatctttg aatttggcag cctgagcaac       360
ccgtatgaaa aatatcgtaa agttgcctat gaacgcctgg tgaatggtct gaaactggtt       420
aaagaagcaa acgccgatat tgcattatt tggcctggta ttgatggcta tacctatagc       480
tatggtcacc tgtattatca catgtgggat acctttgaag aactggttgc acaggcaatg       540
gatgaagttc ggggtgttca ggttgcaatt gaaccgaaac cgtatgaacc ggcaccgaat       600
aacatttatc gtaccaccgc agatggtatt ctggcagcac gtgatattga agcgcgtctg       660
aaaaatccgg aaaacctgaa actgctgcaa gaaggtcacg cactggttgg tctgaatccg       720
gaagttggtc atgttcgtat gggttttgaa gatctgccgt atgcatatgc ccgtgttgca       780
cgtgaaggtc gtctgtttca tacccattgg aatagccagc cgctgggtaa ttatgatcag       840
gatctgaata ttggtgtggt ggattgggat agcaccgaag cactgctgta tacccctgaaa       900 atggttggtt atcagggcta ttttggcatc gatatcaatc cggaacgcat gccggttatt       960
aaagccattg aaattaacac caaagtgctg cagattatga cgaacgcat tgaacgtctg      1020 ccgcatgatc gtattattga gtgttatttt gaccctgaga tcatcgtgg tgaactggaa      1080 ctgattctgg ccgaaaatca taaataa                                         1107

<210> SEQ ID NO 5
<211> LENGTH: 1107
<212> TYPE: DNA
<213> ORGANISM: Dictyoglomus turgidum

<400> SEQUENCE: 5
atgccgtttg tggatcatcg taatcagaaa attcgtcgca gcaaagaaga actgctgaaa        60
catatgcaga ccttcaaact ggatctgaaa tttagcgtgg gcatctggta ttttacaccg       120
ggtggtggtc gttttcatga accgtatgtt gaacagaaag gtattccgga acgtattgaa       180
atggcagcag aaatggcaaa atatggcgtt aaaggtatcg aagcacatta tccggctgaa       240
gtgaatgaag aaaatctgca cctgtataaa cagctggaaa agaaaccgg tattcgtctg       300 gttgcagttc cgctgagcct gttttatgat aaaatctttg aatttggcag cctgagcaac       360
ccgtatgaaa aatatcgtaa aattgcctat gaacgcctgg tgaatggtct gaaactggtt       420
```

```
aaagaagcaa acgccgatat ttgcattatt tggcctggta ttgatggcta tacctatagc    480
tatggtcacc tgtattatca catgtgggat acctttgaag aactggttgc acaggcaatg    540
gatgaagttc cgggtgttca ggttgcaatt gaaccgaaac cgtatgaacc ggcaccgaat    600
aacatttatc gtaccaccgc agatggtatt ctggcagcac gtgatattga agcacgtctg    660
aaaaatccgg aaaacctgaa actgctgcaa gaaggtcacg cactggttgg tctgaatccg    720
gaagttggtc atgttcgtat gggttttgaa gatctgccgt atgcatatgc ccgtgttgca    780
cgtgaaggtc gtctgtttca tacccattgg aatagccagc cgctgggtaa ttatgatcag    840
gatctgaata ttggtgtggt ggattgggat agcaccgaag cactgctgta tacccctgaaa   900 atggttggtt atcagggcta ttttggcatc gatattaatc cggaacgcat tccggttgtt    960
aaagccattg aaattaacac caaagtgctg cagattatga cgaacgcat tgaacgtctg     1020 ccgcatgatc gtattattga gtgttatttt gaccctgaga atcatcgtgg tgaactggaa    1080
ctgattctgg ccgaaaatca tcgttaa                                        1107
```

<210> SEQ ID NO 6
<211> LENGTH: 1335
<212> TYPE: DNA
<213> ORGANISM: Thermotoga Neapolitana

<400> SEQUENCE: 6

```
atggcagaat ttttcccgga aattccgaaa gttcagtttg aaggtaaaga agcaccaat     60 ccgctggcct ttaaattcta tgatccggaa gaaatcattg acggcaaaac cgctgaaagat   120 catctgaaat ttagcgttgc attttggcac acctttgtga tgaaggtcg tgatccgttt    180 ggtgatccga ccgcagatcg tccgtggaat cgttataccg atccgatgga taaagcattt    240
gcacgtgttg atgcactgtt tgaattttgc gaaaaactga catcgagta tttctgcttt    300 cacgatcgcg atattgcacc ggaaggtaaa accctgcgtg aaaccaacaa aattctggat    360
aaagtggtga acgcatcaa agaacgtatg aaagatagca atgttaaact gctgtggggc    420 accgcaaaacc tgtttagcca tccgcgttat atgcatggtg cagcaaccac ctgtagcgca    480 gatgttttg cctatgcagc agcacaggtt aaaaaagcac tggaaatcac caaagaactg    540
ggtggtgaag ttatgttttt tgggggtggt cgtgaaggct atgaaacact gctgaatacc    600
gatctgggtt ttgaactgga aaatctggca cgttttctgc gtatggcagt tgattatgca    660
aaacgcattg gttttaccgg tcagtttctg attgaaccga aaccgaaaga accgaccaaa    720
caccagtatg attttgatgt tgcaaccgcc tatgcctttc tgaaaagtca tggtctggat    780
gagtacttca aatttaacat cgaagcaaat catgcaaccc tggcaggtca taccttttcag   840 catgaactgc gcatggcacg cattctgggt aaactgggta gcattgatgc aaatcagggt    900
gatctgctgc tgggttggga tacagatcag tttccgacca tgtttatga taccacccctg    960 gcaatgtatg aagttattaa agcaggcggt tttaccaaag gtggcctgaa ttttgatgcc    1020
aaagttcgtc gtgcaagcta taagttgag gacctgttta ttggtcatat cgcaggtatg    1080
gatacctttg cactgggttt taagttgcc tacaaactgg ttaaagatgg cgtgctggat    1140
aaattcatcg aagaaaaata tcgcagcttt cgcgaaggta ttggtcgtga tattgttgaa    1200
ggcaaagtgg attttgagaa actggaagag tacatcatcg ataaagaaac cattgaactg    1260
ccgagcggca acaagaata tctggaaagc ctgattaaca gctacatcgt gaaaaccatt    1320
ctggaactgc gttaa                                                    1335
```

<210> SEQ ID NO 7
<211> LENGTH: 388
<212> TYPE: PRT
<213> ORGANISM: Streptomyces murinus

<400> SEQUENCE: 7

```
Met Ser Phe Gln Pro Thr Pro Glu Asp Arg Phe Thr Phe Gly Leu Trp
1               5                   10                  15

Thr Val Gly Trp Gln Gly Arg Asp Pro Phe Gly Asp Ala Thr Arg Pro
            20                  25                  30

Ala Leu Asp Pro Val Glu Thr Val Gln Arg Leu Ala Glu Leu Gly Ala
        35                  40                  45

Tyr Gly Val Thr Phe His Asp Asp Leu Ile Pro Phe Gly Ser Ser
    50                  55                  60

Asp Thr Glu Arg Glu Ser His Ile Lys Arg Phe Arg Gln Ala Leu Asp
65                  70                  75                  80

Ala Thr Gly Met Thr Val Pro Met Ala Thr Thr Asn Leu Phe Thr His
                85                  90                  95

Pro Val Phe Lys Asp Gly Gly Phe Thr Ala Asn Asp Arg Asp Val Arg
            100                 105                 110

Arg Tyr Ala Leu Arg Lys Thr Ile Gly Asn Ile Asp Leu Ala Ala Glu
        115                 120                 125

Leu Gly Ala Lys Thr Tyr Val Ala Trp Gly Gly Arg Glu Gly Ala Glu
    130                 135                 140

Ser Gly Gly Ala Lys Asp Val Arg Asp Ala Leu Asp Arg Met Lys Glu
145                 150                 155                 160

Ala Phe Asp Leu Leu Gly Glu Tyr Val Thr Ala Gln Gly Tyr Asp Leu
                165                 170                 175

Arg Phe Ala Ile Glu Pro Lys Pro Asn Glu Pro Arg Gly Asp Ile Leu
            180                 185                 190

Leu Pro Thr Val Gly His Ala Leu Ala Phe Ile Glu Arg Leu Glu Arg
        195                 200                 205

Pro Glu Leu Tyr Gly Val Asn Pro Glu Val Gly His Glu Gln Met Ala
    210                 215                 220

Gly Leu Asn Phe Pro His Gly Ile Ala Gln Ala Leu Trp Ala Gly Lys
225                 230                 235                 240

Leu Phe His Ile Asp Leu Asn Gly Gln Ser Gly Ile Lys Tyr Asp Gln
                245                 250                 255

Asp Leu Arg Phe Gly Ala Gly Asp Leu Arg Ala Ala Phe Trp Leu Val
            260                 265                 270

Asp Leu Leu Glu Thr Ala Gly Tyr Glu Gly Pro Arg His Phe Asp Phe
        275                 280                 285

Lys Pro Pro Arg Thr Glu Asp Phe Asp Gly Val Trp Ala Ser Ala Ala
    290                 295                 300

Gly Cys Met Arg Asn Tyr Leu Ile Leu Lys Asp Arg Ala Ala Ala Phe
305                 310                 315                 320

Arg Ala Asp Pro Glu Val Gln Glu Ala Leu Arg Ala Ala Arg Leu Asp
                325                 330                 335

Gln Leu Ala Gln Pro Thr Ala Ala Asp Gly Leu Asp Ala Leu Leu Ala
            340                 345                 350

Asp Arg Ala Ala Phe Glu Asp Phe Asp Val Asp Ala Ala Ala Ala Arg
        355                 360                 365
```

```
Gly Met Ala Phe Glu His Leu Asp Gln Leu Ala Met Asp His Leu Leu
    370                 375                 380

Gly Ala Arg Gly
385
```